United States Patent
Håkansson et al.

(10) Patent No.: US 8,183,430 B2
(45) Date of Patent: May 22, 2012

(54) ABSORBENT ARTICLE

(75) Inventors: Carin Håkansson, Billdal (SE); Anna Klinte Olsson, Askim (SE); Kent Hermansson, Västra Frölunda (SE); Elisabeth Boissier, Vallda (SE)

(73) Assignee: SCA Hygiene Products AB, Gothenburg (SE)

( * ) Notice: Subject to any disclaimer, the term of this patent is extended or adjusted under 35 U.S.C. 154(b) by 581 days.

(21) Appl. No.: 12/086,594

(22) PCT Filed: Dec. 15, 2005

(86) PCT No.: PCT/SE2005/001948
§ 371 (c)(1),
(2), (4) Date: Apr. 8, 2009

(87) PCT Pub. No.: WO2007/069958
PCT Pub. Date: Jun. 21, 2007

(65) Prior Publication Data
US 2010/0036355 A1    Feb. 11, 2010

(51) Int. Cl.
*A61F 13/15* (2006.01)
(52) U.S. Cl. .................. 604/378; 604/385.101; 604/380; 604/379; 604/385.201; 604/385.03; 604/374
(58) Field of Classification Search ............. 604/378, 604/379, 380, 385.01, 385.04, 385.03, 385.101, 604/385.201
See application file for complete search history.

(56) References Cited

U.S. PATENT DOCUMENTS

| | | | |
|---|---|---|---|
| 4,608,047 A | 8/1986 | Mattingly | |
| 4,773,905 A | 9/1988 | Molee et al. | |
| 5,795,344 A | 8/1998 | Chappell | |
| 6,306,123 B1 | 10/2001 | Salerno et al. | |
| 6,448,465 B1 | 9/2002 | Gustafsson | |

FOREIGN PATENT DOCUMENTS

| | | |
|---|---|---|
| EP | 0 304 957 B1 | 3/1989 |
| EP | 0 781 537 A1 | 7/1997 |
| EP | 1 245 211 | 10/2002 |
| EP | 1 332 742 A1 | 8/2003 |
| JP | 2002-238948 | 8/2002 |
| RU | 2 203 009 | 4/2003 |
| WO | WO 92/10984 | 7/1992 |
| WO | WO 00/32146 | 6/2000 |
| WO | WO 01/24754 | 4/2001 |

OTHER PUBLICATIONS

An English Translation of Decision on Grant issued in corresponding Russian Application No. 2008128813.
International Search Report for PCT/SE2005/001948 dated Jul. 11, 2006.
Written Opinion of the International Search Authority for PCT/SE2005/001948 dated Jul. 11, 2006.
Hakansson et al., "Absorbent Article" Application No. 12/086,612, filed on Jun. 16, 2008.
Decision on Grant issued in corresponding Russian Application No. 2008128829.

*Primary Examiner* — Jacqueline F. Stephens
(74) *Attorney, Agent, or Firm* — Buchanan Ingersoll & Rooney PC (57) ABSTRACT

An absorbent article, especially an incontinence pad, having a length and a width extension, the length being greater than the width, and including absorbent core material, wherein the absorbent core material forms a central portion (6) and a pair of longitudinally extending side portions (7), the flexural rigidity of the article (1) at the side portions (7) is between 3 and 20% of the flexural rigidity of the article (1) of the central portion (6) at a location opposite the side portions (7), preferably between 4 and 15%, most preferred between 4 and 10%.

33 Claims, 5 Drawing Sheets

ABSORBENT ARTICLE

FIELD OF INVENTION

The present disclosure relates to an absorbent article, having a length and a width extension, said length being greater than said width and comprising absorbent core material. The absorbent article can be a sanitary napkin, a panty liner, an incontinence pad or the like. The invention is especially useful for an incontinence pad.

TECHNICAL BACKGROUND

Absorbent articles of the above mentioned kind are intended to absorb body liquids such as urine and blood. To this end, the articles are worn close to the wearer's body and usually placed in the wearer's underwear. For the comfort of the wearer and for the most efficient use of the article, it is thus of importance that the article may adjust well to the wearer's body.

Flexible articles generally have the advantage of adapting to the user's body, since they will be easily compressible. However, flexible articles may have the disadvantage that after compression e.g. between the thighs of the user, they cannot sufficiently fill the space there between, which might result in unwanted leakage at the longitudinal edges of the article. Relatively flexible products further have a tendency that the compression will result in the article having a series of folding lines or creases.

Stiffer articles might maintain their structural integrity better than more flexible products, but may have the disadvantage of being perceived as more uncomfortable. Also, stiffer articles may, once they do become compressed, be compressed substantially along one line only, giving rise to a V-shaped article which may be subject to leakage problems similarly to more flexible products. In use, this type of product will normally fold such that, in use, the shape corresponds to an inverted V between the thighs of the user.

A known article in the form of an incontinence pad is formed in an elongate shape having parallel longitudinal edges. The longitudinal edges at the centre portion of the product are provided with an elastic material which functions so as to pull the longitudinal ends of the article towards each other, resulting in a longitudinally cup-shaped article thus intended to conform to the body of the wearer. Further, the longitudinal edges having the elastic material will extend upwardly so as to form an arc-shaped article also in a transverse direction thereof, at least at the centre portion of the article. This feature may act so as to diminish the risk of leakage of body fluids.

Although well functioning for many users, some users of the above-mentioned article report that the regions of elastic material, when absorbing body liquid, might feel humid. Further, there might be a risk of leakage at the sides of the product.

JP2002238948 describes an absorbent article such as a sanitary napkin, an incontinence pad, a panty liner or the like. The article comprises an absorbent having an upper absorber and a smaller sized lower absorber laminated to the back side of the upper absorber. Grooves are formed on the part corresponding to the lower absorber on the upper absorber. Hence, the upper absorber may be projected upwardly at the part thereof being positioned on the lower absorber. Hence, the product may form a downwardly directed arc-shape in a transverse direction thereof.

Thus, there is a need for an absorbent article, in particular an incontinence pad, which may adapt to the wearer's body and which limits the problems of humidity and/or leakage.

OBJECT AND SUMMARY

One object is to provide an absorbent article which adapts well to the wearer's body and diminishes any leakage problems. Further, the article should preferably be suitable as an incontinence pad.

The above-mentioned object is achieved by an absorbent article, especially an incontinence guard having a length and a width extension, said length being greater than said width, and comprising absorbent core material, wherein the flexural rigidity of the side portions is between 3 and 20% of the flexural rigidity of the article (1) of the central portion (6) at a location opposite the side portions (7), preferably between 4 and 15%, most preferred between 4 and 10%.

The flexural rigidities are measured according to the method as will be described later on in the application.

It has been found, that the above relationship between the rigidity of the side portions and the central portion of the article results in an article where the side portions will deform prior to the central portion, such that the side portions enable the required adaptation to the body of the user, whereas the central portion maintains sufficient structural integrity to diminish any leakage problems.

Advantageously, the flexural rigidity of the article at the side portions may be between 0.35 and 1.1. Advantageously, the flexural rigidity of the article at the central portion at a location opposite the side portions is between 6.5 and 10.1. The measurements are made in accordance with the method as described herein.

Advantageously, the thickness of the article at of the side portions is less than the thickness of the central portion at a location opposite the side portions. Thus, the side portions will be more easily foldable than the central portion, such that the desired form of the article when in use is achieved.

In this case, it has been found to be suitable that the thickness of article at the side portions may be between 40 and 80% of the thickness of the article at the central portion at a location opposite the side portions, preferably between 50 and 70%, most preferred between 55 and 65%.

Preferably, the absorbent article may comprise a pair of folding lines being provided so as to divide said absorbent core material into said central portion and said pair of longitudinal side portions. The folding lines have the advantage that the site of folding of the article when in use may be controlled, which contributes to the desired deformation of the product.

The folding lines are generally lines being provided so as to facilitate the folding of the side portions. Advantageously, the folding lines may be formed by compression of the absorbent material.

The folding lines may completely separate the absorbent material in the side portions from the absorbent material in the central portion.

Alternatively, the folding lines may only partly separate the absorbent material in the side portions from the absorbent material in the central portion.

Preferably, the folding lines are positioned and extending along a length such that, when the article is in use, the folding lines are generally positioned so as to extend along the crotch area of the user, starting from the gracilis tendons and ending in the region of the perineum, whereby the side portions may extend from the central portion towards the user so as to form an arc shape as seen in a transversal direction of the article.

Hence, the start and end positions of the folding lines are suitable for placement at the gracilis tendons of a user and in the region of the perineum of a user, respectively. Further, the folding lines enables the side portions of the article to fold so as to adapt to the body of the user along the crotch area between the gracilis tendons and the region of the perineum, without unnecessarily effecting the width extension of the product at the central portion, which may extend in front and behind the pair of side portions. Thus, adaptation to the wearer's body is generally provided in the centre region of the article, where this is most wanted. At the same time, the front and back region of the article is not adversely affected by the adaptation of the middle region.

Advantageously, the folding lines may be extending concavely along the article, so as to provide a shape being suitable for fitting to the body of a user.

Preferably, the folding lines have a length of about 60 to 170 mm, preferably 80 to 140 mm, most preferred 90 to 130 mm.

The folding lines may advantageously extend along about ⅓ of the total length of the article.

The folding lines are generally lines being provided so as to facilitate the folding of the side portions. Advantageously, the folding lines may be formed by compression of the absorbent material. The compression lines may extend e.g. wholly or partly through the absorbent core only, through the absorbent core and the topsheet material, or through the absorbent core, a topsheet material and a backsheet material.

The folding lines may completely separate the absorbent material in the side portions from the absorbent material in the central portion.

Alternatively, the folding lines may only partly separate the absorbent material in the side portions from the absorbent material in the central portion.

In a preferred embodiment, the outer longitudinal edges of said absorbent material forms three convex lobes,
  said pair of folding lines extend concavely between the longitudinal ends of the middle one of said three lobes,
  so as to divide the absorbent core material into a central portion and a pair of longitudinal side portions,
  such that, when the article is in use, the folding lines are generally positioned so as to along the crotch area of the user, starting from the gracilis tendons and ending in the region of the perineum, whereby the side portions may extend from the central portion towards the user so as to form an arc shape as seen in a transversal direction of the article.

The three-lobe shape of the article is well adjusted to the body of a wearer in that the two indentations (of concave shape) being formed between the first and middle lobes, and the middle and third lobe, are suitable for placement at the gracilis tendons of a user and in the region of the perineum of a user, respectively. Further, the concave folding lines enable the side portions of the article to fold so as to adapt to the body of the user along the crotch area between the gracilis tendons and the region of the perineum, without unnecessarily affecting the width extension of the product at the first and third lobes, being positioned in front and at the back of said crotch area. Thus, adaptation to the wearer's body is generally provided in the centre region of the article, where this is most wanted. At the same time, the front and back region of the article is not adversely affected by the adaptation of the middle region.

The folding lines are such that side portions may extend from the central portion towards the user so as to form an arc shape as seen in a transversal direction of the article. This configuration of the article is believed to be the most advantageous in order to diminish leakage from the product. However, it is not excluded that the side portions may alternatively extend from the central portion away from the user. In this configuration, the adaptation to the user's body is achieved, which also contributes to diminishing the leakage problems.

The three-lobe shape of the article has the additional advantage that it may be adapted so as to provide efficient use of the starting materials for manufacture of the article. Such starting materials are generally web-shaped with a constant width. With a three-lobe shape, the material waste during manufacture may be kept relatively low which contributes to the cost-effectiveness and environmental-friendliness of the article.

To achieve a good fit with the tendons of the wearer, the length between the longitudinal ends of the middle lobe may be about 60 to 170 mm, preferably 80 to 140 mm, most preferred 90 to 130 mm.

Advantageously, the middle lobe may extend along about ⅓ of the total length of the article. Preferably, the front and back lobe will then also extend along about ⅓ of the total length, such that each lobe extends along about ⅓ of the total length of the article.

The maximum width of the middle lobe may be between 60 and 150 mm, preferably between 70 and 130 mm, most preferred between 80 and 120 mm. Further, the maximum width of the middle lobe divided by the width of the absorbent core at one of the ends of said middle lobe may advantageously be between 110 and 180%, preferably 110 and 150%, most preferred 110 and 130%. Advantageously, the distance between the maximum width of the middle lobe and the adjacent folding line is less than 30 mm, preferably in the range 10 to 30 mm, most preferred in the range 15 to 25 mm.

The measures and proportions as mentioned above have been found to provide particularly good adjustment to the body of a wearer.

Preferably the minimum width of the article is the width as measured at either of the ends of the middle lobe. Hence, the minimum width of the article is the width where the folding lines start and/or begin. This configuration is advantageous in order to provide the required room for the user's body e.g. at the gracilis tendons and the region of the perineum. In this context, the minimum width refers to the width along the essential length of the article. It is possible that the width of the product become somewhat narrower at the end of the product, where the article width might successively diminish.

The widths at the ends of the middle lobe may advantageously be in the range 30 to 100 mm, preferably 40 to 90 mm, most preferred 60 to 85 mm. Suitably, the widths at the two ends of the middle lobe may be essentially the same.

Advantageously, the maximum widths of the three lobes are substantially the same. This particular configuration provides good adjustment to the wearer's body. Further, it is advantageous from a manufacturing point of view. Since the starting materials for manufacturing the article are generally band-shaped, the width of the bands may be selected to conform to the maximum width of the product being the width of the three lobes. Hence, very small amounts of material will be wasted during manufacture of the product.

Absorbent articles are often provided with an adhesive at a garment facing side thereof, so as to enable attachment to the underwear of a user. Advantageously, a garment facing side of the article may be free from adhesive at the side portions. Thus, the folding of the side portions is not restricted by the shape or elasticity of the undergarment.

Preferably, the absorbent core material may comprise an upper absorbent core and a lower absorbent core. "Upper" as used herein relates to the direction of the product intended to be positioned closer to the wearer when in use, whereas "lower" as used herein relates to the direction of the product closer to the garment-facing side thereof.

Preferably, the absorbent core material may comprise an upper absorbent core and a lower absorbent core. "Upper" as used herein relates to the direction of the product intended to be positioned closer to the wearer when in use, whereas "lower" as used herein relates to the direction of the product closer to the garment-facing side thereof.

Advantageously, one of the upper and lower absorbent core may be wider than the other as measured at the middle lobe of the article. In this configuration, the side portions will comprise at least an area including absorbent material from the widest of the cores only. This is believed to be beneficial for folding of the side portions of the article when in use.

In one embodiment, the lower absorbent core may be wider than the upper absorbent core as measured at the middle lobe of the article. In this configuration, side portions will comprise at least an area including absorbent material from the lower absorbent core only. This is believed to be beneficial for upward folding of the side portions of the article when in use.

Preferably, one of the upper and lower absorbent core may be wider than the other as measured at the middle lobe of the article, and the folding lines may extend along the least wide of the cores, such that the side portions essentially comprise absorbent material from the widest of the cores only. Hence, controlled folding of the side portions is facilitated.

If the lower absorbent core is wider than the upper absorbent core as measured at the middle lobe of the article, the folding lines may preferably extend along the longitudinal sides of the upper absorbent core, such that said side portions essentially comprise absorbent material from the second absorbent core only.

It may be understood, that it is generally desired that the side portions may be folded along the folding lines, whereas the central portion of the article in between the folding lines may be kept relatively smooth. This contributes to the above-mentioned effect that the central portion structure is kept relatively unaffected by the adjustment to the body, which is performed by the side portions. Hence, the stability and stable positioning of the article may be ensured.

Advantageously, one of the upper and lower absorbent cores may be longer than the lower absorbent core as measured in the longitudinal direction of the article. In this configuration a maximum amount of absorbent core material is provided near to the centre of the product. Further, the longitudinal end portions of the product are relatively thin, which contributes to the comfort and aesthetics of the product when in use.

Preferably, one of the absorbent cores may be generally hour-glass shaped (also called "dog-bone-shaped"). This shape is particularly suitable also for the centre portion of the absorbent material, as it is well suited to fit between the wearer's legs. Hence, the first convex lobe, the concave folding lines and the third convex lobe may together form an hour-glass shape.

Advantageously, the other one of the absorbent cores is generally circular or oval. This shape enables the convex middle lobe of the product to be formed by the circular or oval edges of the lower absorbent core.

When using an upper and a lower absorbent core, the thickness of said side portions may include the thickness of the widest one of the upper and lower absorbent core, and the thickness of the central portion at a location opposite the side portions may include the thickness of the lower absorbent core plus the thickness of the upper absorbent core.

The method used for measuring flexural rigidity will be described in the following detailed description.

BRIEF DESCRIPTION OF THE DRAWINGS

Preferred embodiments of the invention will be described in the following in greater detail by way of example and with reference to the accompanying drawings, in which.

DETAILED DESCRIPTION OF PREFERRED EMBODIMENTS

The following examples or provided for illustrative purposes only and are not intended to limit the scope of the invention in any way.

The term "absorbent article" refers to products that are placed against the skin of the wearer to absorb and contain body exudates, like urine, and menstrual fluid. The disclosure mainly refers to disposable absorbent articles, which means articles that are not intended to be laundered or otherwise restored or reused as an absorbent article after use.

Figure 1:
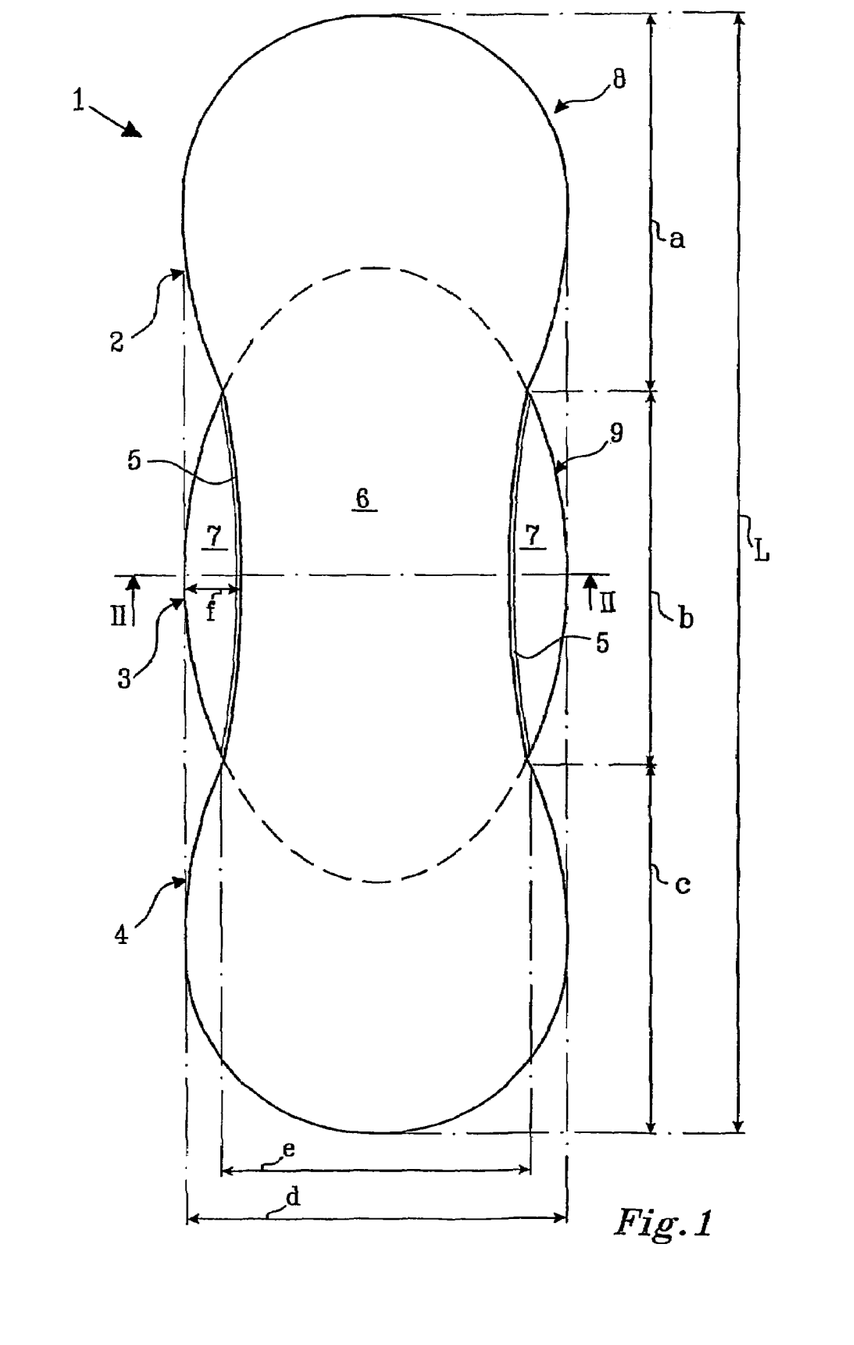
FIG. 1 is a schematic view from above of an absorbent article according to one embodiment of the invention.

FIG. 1 illustrates an absorbent article in the form of an incontinence pad 1. In its most common form the absorbent article comprises an absorbent core and a cover enclosing the absorbent core. The cover comprises a liquid pervious topsheet on the wearer facing side of the absorbent core and a liquid barrier backsheet material on the garment facing side of the absorbent core.

Details regarding the general construction of various layer sheets will be described in more detail later on in relation to FIG. 4.

The article 1 of FIG. 1 has a length and a width extension, wherein the total length (L) is greater than the maximum width (d). The article 1 comprises, as is conventional in the art, absorbent core material.

As illustrated in FIG. 1, the outer longitudinal edges of the absorbent material form three convex lobes 2, 3, 4; a first lobe 2, a middle lobe 3, and a third lobe 4. A pair of folding lines 5 extend concavely between the longitudinal ends of the middle one 3 of said three lobes 2, 3, 4, so as to divide the absorbent core material into a central portion 6 and a pair of longitudinal side portions 7.

When the article 1 is in use, the folding lines 5 are generally positioned so as to extend along the crotch area of the user, starting from the gracilis tendons and ending in the region of the perineum, whereby the side portions 7 may extend from the central portion 6 towards the user so as to form an arc shape as seen in a transversal direction of the article 1.

In the illustrated embodiment, the lengths a, b, c of the three lobes 2, 3, 4 are generally equal and approximately ⅓ of the total length L of the product. With this configuration, the product is symmetrical and so can be used with either of the first 2 and the third lobe 4 as the front end.

Regarding the length b between the longitudinal ends of the middle lobe 3, this is in the illustrated embodiment about 11 cm, whereas the total length of the product is about 33 cm. As explained above, these lengths may vary within suitable intervals. The total length of the product may for example vary between 15 and 45 cm.

It is understood that with the ends of the lobes is meant the ends of the respective convex portion of the longitudinal edges of the absorbent material. Hence, the length b of the middle lobe is measured from the midst of the concave portions formed in-between the three convex lobes. Since the concave portions between the lobes will function to accommodate the user's body, e.g. the gracilis tendons of the user and the perineum region, the distance between the concave portions, and hence the length of the middle lobe, should preferably be adapted to this anatomical distance.

In the illustrated embodiment, the maximum width (d) of the middle lobe (3) is about 10 cm. Further, in this case, the maximum widths (d) of all three lobes are the same. The width (e) of the article as measured at one of the ends of the middle lobe, in this case being the minimum width of the product, is about 8 cm.

(From the exemplified dimensions, it is understood that the side portions 7 of the absorbent core material are different from structures commonly referred to as "wings" or "flaps" and provided in prior art products in order to ensure fastening to the undergarment. Wings or flaps are generally dimensioned to be folded around and fastened to the wearer's undergarment.)

As illustrated in FIG. 1, two folding lines 5 are formed extending concavely along the article between the ends of the middle lobe 3. The folding lines are intended to facilitate the folding of the side portions 7 of the core in relation to the central portion 6.

In the illustrated embodiment, the folding lines 5 are formed by compression of the absorbent material. In this case, the compression lines 5 extend to a depth in the absorbent material so as to provide an indentation or groove forming the compression line, but not so deep as to completely separate the absorbent material in side portions 7 from the absorbent material in the central portion 6 (See FIG. 2). Hence, the compression lines in this case only partly separate the absorbent material in the side portions 7 from the absorbent material in the central portion 6. In this embodiment, body fluid absorbed by the absorbent material may thus travel in the absorbent material from the side portions 7 towards the central portion 6 or vice versa.

However, other embodiments are possible in which the compression lines may extend all the way through the absorbent material so as to completely separate the absorbent material in the side portions 7 from the central portion 6.

Further, regardless of whether the compression lines extend to a depth being equal to the depth of the absorbent material or not, the compression lines may be continuous, as in the illustrated embodiment, or discontinuous (a broken or dashed line).

Selection between the different alternatives of compression lines may be made taking the fluid distribution in the absorbent material as well as the required tendency of the side portions to fold into consideration.

The fluid distribution in the product may be delayed by the use of compression lines as a temporary barrier against flow.

The compression lines may be made in the absorbent core only, or extending into other components of the product such as a top sheet and/or a backsheet.

In order for the compression line to be useful as a folding line, the compression may preferably extend into the absorbent core material. Advantageously, the compression line may extend to a depth corresponding to at least 20% of the core depth, preferably at least 50%, most preferred at least 75%.

Examples of compression lines that may be used in this context may be found in EP 0 781 537 A1, U.S. Pat. No. 5,795,344, EP 1 332 742 A1, and WO 00/32146.

The absorbent core material of the illustrated embodiment comprises an upper absorbent core 8 and a lower absorbent core 9. The lower absorbent core will be closer to a garment facing side of the article than the upper absorbent core.

In FIG. 1 the shapes of the upper absorbent core 8 (whole line) and the lower absorbent core 9 (broken line) are illustrated. In this case, the upper absorbent core 8 is hour-glass shaped, whereas the lower absorbent core 9 is generally oval.

The lower absorbent core 9 is thus wider than the upper absorbent core 8 as measured at the middle lobe of the article. In particular, the widest portion of the oval of the lower absorbent core is positioned in line with the waist of the upper absorbent core 8. Hence, the middle convex lobe 3 of the article will be formed by the lower absorbent core 9, and the first 2 and second 4 convex lobes are formed by the two wider sections of the hour-glass shape of the upper absorbent core 8.

The folding lines 5 will in this case extend along the longitudinal sides of the upper absorbent core 8 so as to follow the shape of the waist of the hour-glass. Hence, the side portions 7 will comprise absorbent material from the second absorbent core 8 only.

Further, the upper absorbent core 8 is longer than the lower absorbent core 9 as measured in the longitudinal direction of the article 1. Hence, the centre region of the central portion 6 of the article will contain the maximum amount of absorbent material, which is suitable since this area is the general area of impact of body fluids. The front and back regions of the article will be somewhat thinner than the centre region, which contributes to a comfortable product without unnecessary bulk.

The lower absorbent core 9 being wider than the upper absorbent core 8 and essentially forming the side portions 7 has the additional advantage that the product, when in use, will have an increased tendency to form such that the side portions 7 extend upwards towards the wearer.

In the illustrated embodiment, the thickness of the article at of the side portions 7 is less than the thickness of the central portion 6 at the middle lobe 3, since the side portions 7 include absorbent material of the lower core 9 only, whereas the central portion 6 at the middle lobe 3 includes material from the upper core 8 and the lower core 9.

The thickness of the side portions 7 being less than the thickness of the central portion 6 at the middle lobe 3 contributes to the tendency of the side portions 7 to fold and deform rather than the central portion 6. The desired difference in thickness may in other embodiments be obtained using only one absorbent core, or using more than two cores.

In the exemplified embodiment, the thickness of the central portion 6 is about 11 mm, and the thickness of the wings is about 7 mm, although these dimensions may of course be varied for different types or sizes of product.

In order to control the deformation of the article 1 when in use, such that the side portions 7 will fold and deform rather than the central portion 6, it has been found that the flexural rigidity of the side portions 7 in relation to the central portion 6 at the middle lobe 3 is of importance.

In particular, the flexural rigidity as measured in a cross-direction of the article at the side portions 7 and of the central portion 6 has been found to be relevant in order to provide a product where the deformation takes place mainly at the side portions 7.

"Flexural rigidity" as used herein refers to measures obtained by the flexural rigidity test which is described later on in this application.

Advantageously, the flexural rigidity of the article 1 at the side portions 7 is between 3 and 20% of the flexural rigidity of the central portion (6) at the middle lobe (3) of the article (1), as mentioned above. The flexural rigidities are measured according to the method as described herein. In the illustrated embodiment, said flexural rigidity is about 8.7% if using maximum load measures.

Figure 2:
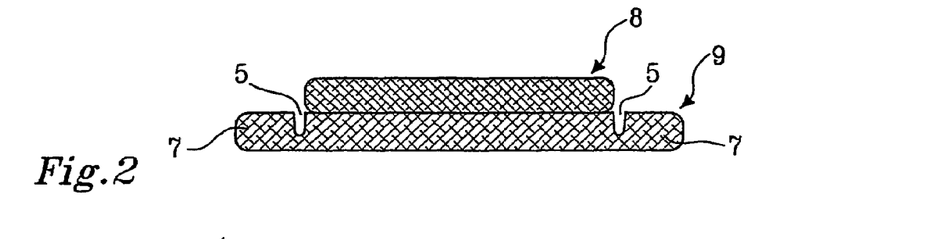
FIG. 2 is a section along the line II-II in FIG. 1, depicting only the absorbent core portion of the article.
Figure 3:
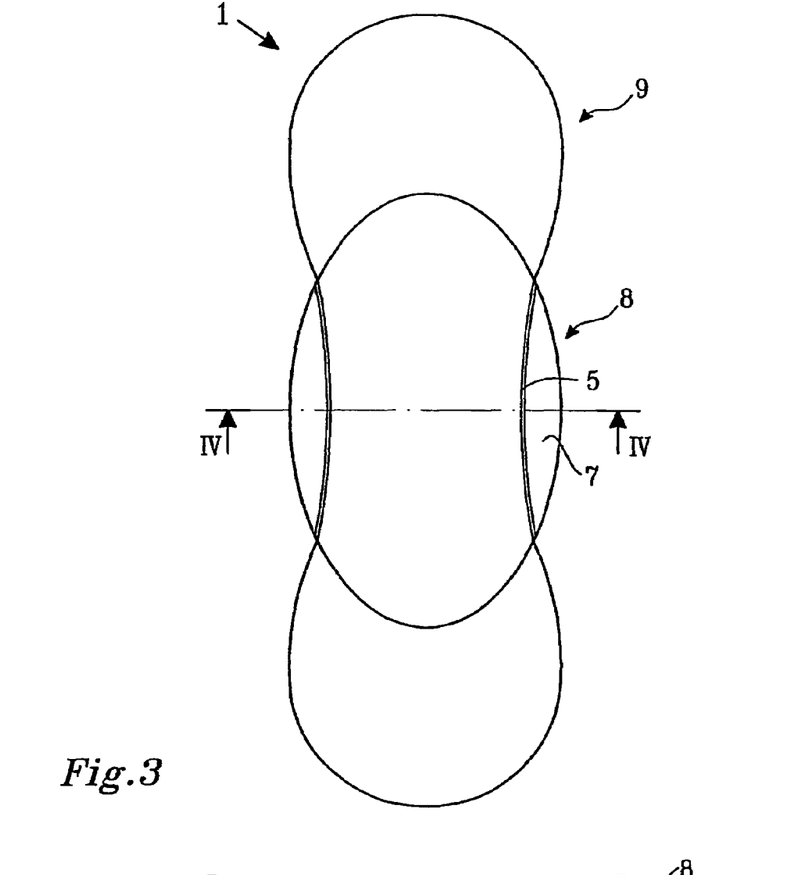
FIG. 3 is a schematic view from above of an absorbent article according to a second embodiment of the invention.
Figure 4:
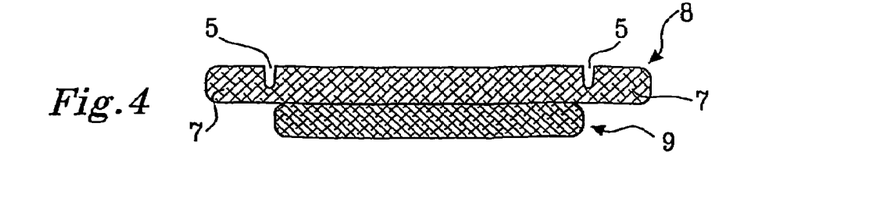
FIG. 4 is a section along the line IV-IV in FIG. 3, depicting only the absorbent core portion of the article.

FIGS. 3 and 4 illustrate schematically a second embodiment of an article. The second embodiment differs from the embodiment of FIGS. 1 and 2 in that the upper core 8 is wider than the lower core 9. Further, the upper core 8 is shorter than the lower core 9. In the illustrated embodiment, the upper core 8 is generally oval shaped, and the lower core 9 is generally hour-glass shaped. This embodiment has an aesthetical advantage in that the side portions 7 will start from the upper portion of the product. The folding lines 5, in this case being compression lines, are formed in the upper core 8, extending along the periphery of the lower core 9.

Apart from the different configuration of the cores, the second embodiment depicted in FIGS. 3 and 4 is similar to the first embodiment described in relation to FIGS. 1 and 2, which is why the features and advantages as set out above in relation to the first embodiment generally apply also to the second embodiment.

Figure 5:
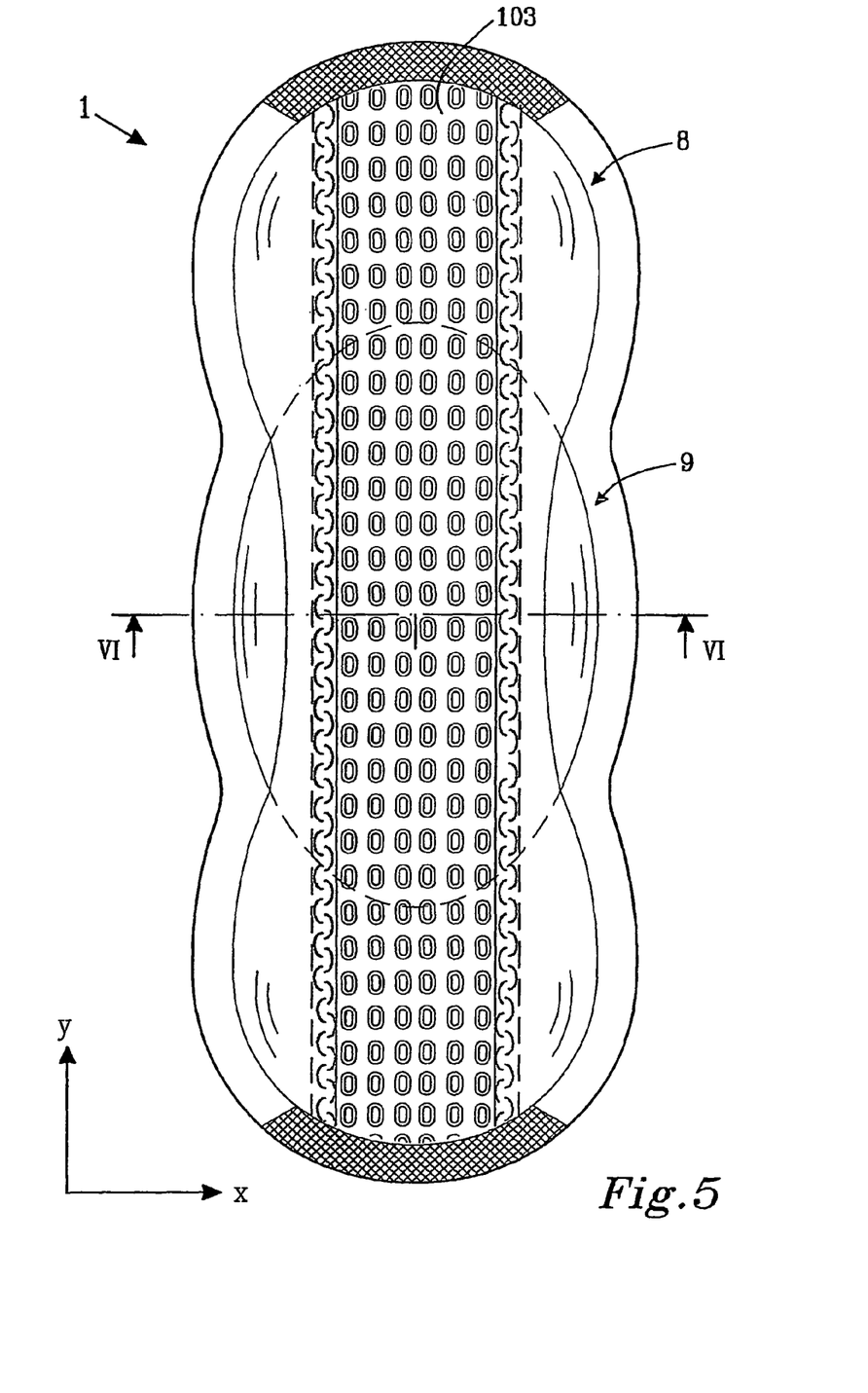
FIG. 5 is a view from above of the article in FIG. 1, but comprising further details regarding the topsheet etc.
Figure 6:
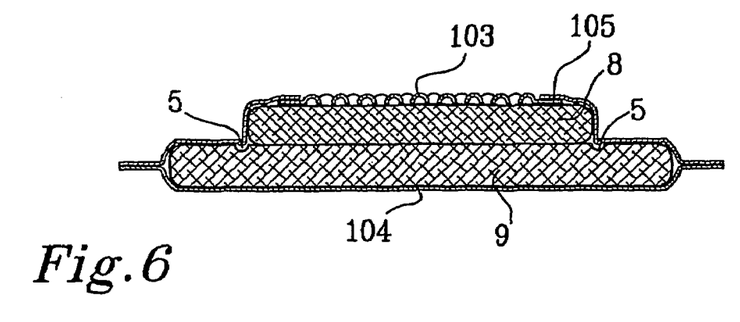
FIG. 6 is a section according to the line VI-VI in FIG. 5.

In FIGS. 5 and 6, the various components of the article of FIGS. 1 and 2 are shown in more detail. (Similar features could be added to the embodiment illustrated in FIGS. 3 and 4.) The absorbent article comprises an absorbent core consisting of the upper absorbent core 8 and the lower absorbent core 9, and a cover enclosing the absorbent core. Said cover comprises a liquid pervious topsheet 103 on the wearer facing side of the absorbent core and a liquid barrier backsheet material 104 on the garment facing side of the absorbent core.

The topsheet 103 forms the inner cover of the absorbent article and in use is placed in direct contact with the skin of the wearer. The topsheet can comprise a nonwoven material, e.g. spunbond, meltblown, carded, hydroentangled, wetlaid etc. Suitable nonwoven materials can be composed of natural fibers, such as woodpulp or cotton fibres, manmade fibres, such as polyester, polyethylene, polypropylene, viscose etc. or from a mixture of natural and manmade fibres. Further examples of inner liquid permeable cover materials are porous foams, apertured plastic films, laminates between apertured films and nonwovens etc. The materials suitable for inner liquid permeable cover materials should be soft and non-irritating to the skin and be readily penetrated by body fluid, e.g. urine or menstrual fluid. The inner liquid permeable cover may further be different in different parts of the absorbent article.

The backsheet material 104 may be a thin plastic film, e.g. a polyethylene or polypropylene film, a nonwoven material coated with a liquid impervious material, a hydrophobic nonwoven material, which resists liquid penetration or a laminate comprising plastic films and nonwoven materials. The backsheet material 104 may be breathable so as to allow vapour to escape from the absorbent core, while still preventing liquids from passing therethrough. Examples of breathable backsheet materials are porous polymeric films, nonwoven laminates from spunbond and meltblown layers, laminates from porous polymeric films and nonwovens.

The absorbent core material can be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbent polymers in an absorbent core. Superabsorbent polymers are water-swellable, water-insoluble organic or inorganic materials capable of absorbing at least about 20 times their weight in an aqueous solution containing 0.9 weight percent of sodium chloride. Organic materials suitable for use as a superabsorbent material can include natural materials such as polysaccharides, polypeptides and the like, as well as synthetic materials such as synthetic hydrogel polymers. Such hydrogel polymers include, for example, alkali metal salts of polyacrylic acids, polyacrylamides, polyvinyl alcohol, polyacrylates, polyacrylamides, polyvinyl pyridines, and the like. Other suitable polymers include hydrolyzed acrylonitrile grafted starch, acrylic acid grafted starch, and isobutylene maleic anhydride copolymers and mixtures thereof. The hydrogel polymers are preferably lightly crosslinked to render the material substantially water insoluble. Preferred superabsorbent materials are further surface crosslinked so that the outer surface or shell of the superabsorbent particle, fiber, flake, sphere, etc. possesses a higher crosslink density than the inner portion of the superabsorbent. The superabsorbent materials may be in any form suitable for use in absorbent composites including particles, fibers, flakes, spheres, and the like.

A high absorption capacity is provided by the use of high amounts of superabsorbent material. For an absorbent core comprising a matrix of hydrophilic fibers, such as cellulosic fibers, and superabsorbent material, the proportion of superabsorbent material is preferably between 10 and 90% by weight, more preferably between 30 and 70% by weight.

The absorbent core may comprise layers of different material with different properties with respect to liquid receiving capacity, liquid distribution capacity and storage capacity. The thin absorbent bodies, which are common in for example baby diapers and incontinence pads, often comprise a compressed mixed or layered structure of cellulosic fluff pulp and superabsorbent polymers. The size and absorbent capacity of the absorbent core may be varied to be suited for different uses such as for infants or for adult incontinent persons.

Other examples of absorption materials useful as absorbent cores are laminates of roll materials, such as airlaid tissue, nonwovens and through-air-dried tissue, and superabsorbent materials, wherein an inner layer or strings of superabsorbent material is present between outer layers of said roll material. The different layers are bonded together by for example glue or by heat bonding.

In the exemplified prior art product, the absorbent core comprises two layers, an upper layer 8 and a lower layer 9. In other embodiments only one layer or three or more layers may be present. Further, each of the "upper layer" 8 and the "lower layer" 9 may comprise one or more material layers.

A liquid transfer layer 105 may be arranged between the topsheet 103 and the absorbent core material. The transfer layer is a porous, resilient, relatively thick material layer, for example in the form of a fibrous wadding, a carded fibrous web, a tow material or other type of bulky and resilient fibrous material having a high momentaneous liquid receiving capacity and which can temporarily store liquid before it is absorbed by the underlying absorbent body. The liquid transfer layer may further be in the form of a porous foam material. It may further consist of two or more material layers. The basis weight of the transfer layer is between 20 and 100 $g/m^2$, preferably between 30 and 80 $g/m^2$.

The absorbent article may be provided with an adhesive at a garment-facing side thereof, so as to enable fastening of the article to the undergarment of a wearer. In this case, the garment facing side of the article 1 is preferably free from adhesive at the side portions 7, such that the side portions 7 are not restricted in their folding by the undergarment.

Flexural Rigidity Test

The method is intended to measure the flexural rigidity or resistance of an article when it is folded in a specific fixture. In the context of this application, the method is used to describe the characteristics of the side portions and the central portion of a product, in order to form an article suitable for adjustment to the shape of the body, when the article is placed in an undergarment. The measurement method has previously been used for thin products such as sanitary napkins with Dry Formed Reel core, panty liners with High Densified Core and panty liners without core.

Figure 7:
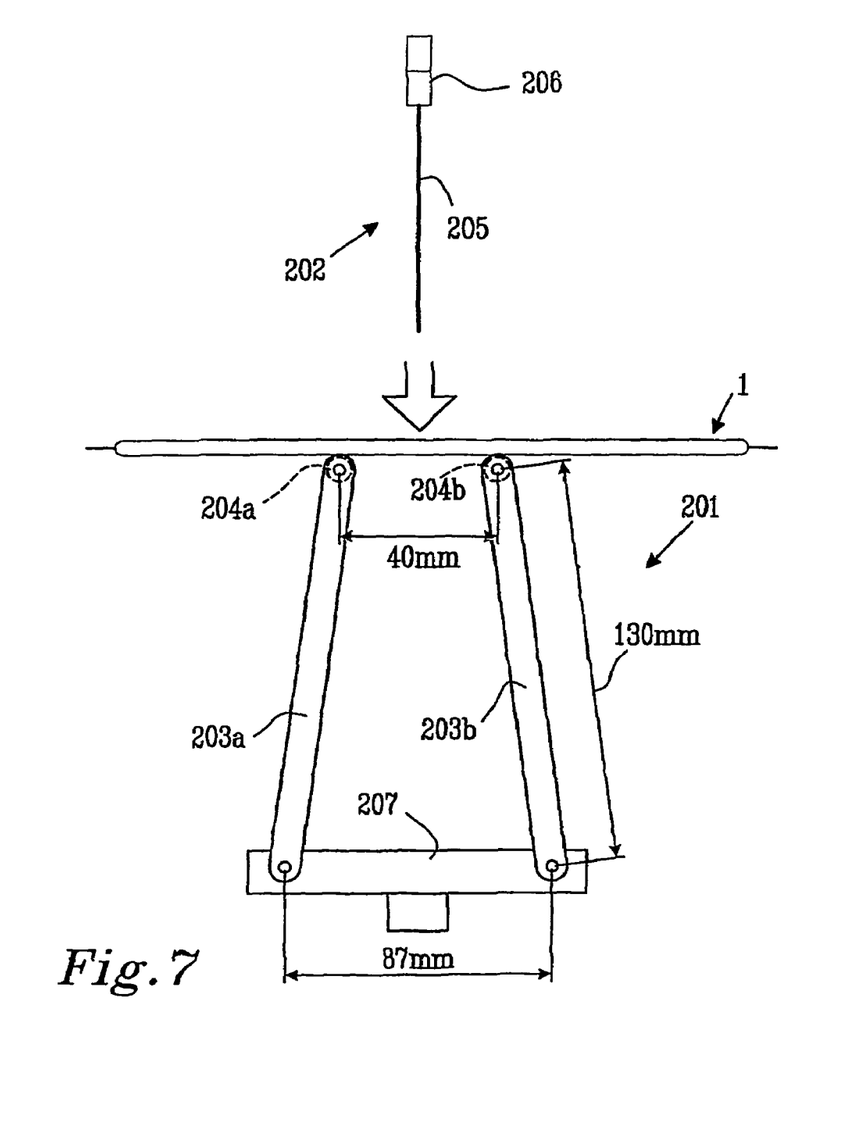
FIGS. 7 and 8 illustrate schematically the testing equipment used for the flexural rigidity test as described herein.
Figure 8:
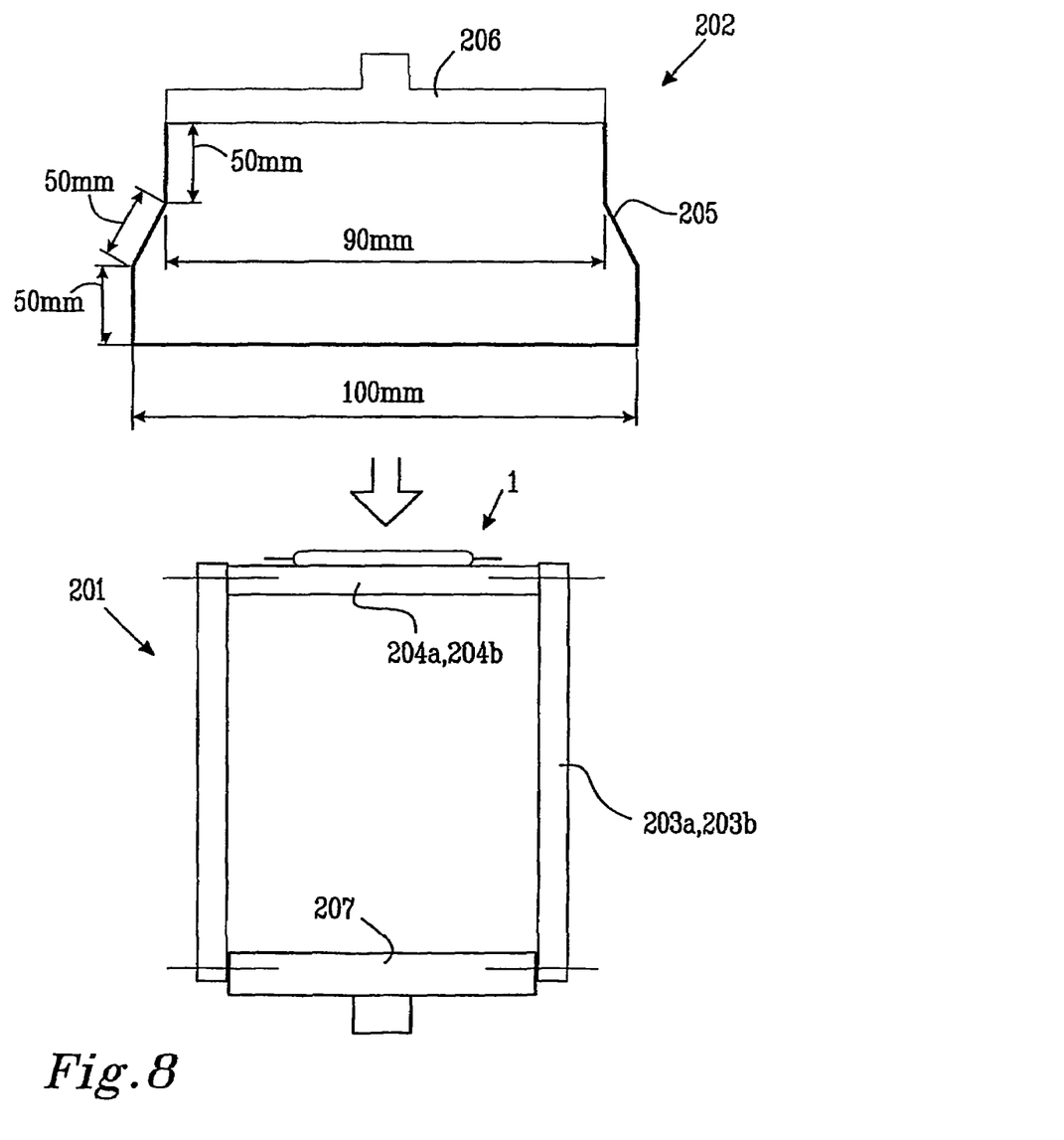

FIG. 7 is a schematic side view of the equipment used for performing the flexural rigidity test. FIG. 8 is another schematic side view of the equipment, as seen perpendicular to the view of FIG. 7.

The equipment comprises a base fixture 201 for supporting an article 1 to be measured, and an upper fixture 202 to be lowered down onto the article 1 when resting on the base fixture 201.

The base fixture 201 comprises a base means 207 including a holder for attachment to a tensile tester. The base means 207 is provided with two support means 203a and 203b. Each support means 203a, 203b comprises two generally vertical bars and a horizontal bar 204 extending horizontally between the two generally vertical bars. The support means 203a, 203b are attached to the base means 207 in a position so as to lean somewhat towards each other. Hence, the distance between the centre of the support means 203a, 203b at the base means 207 is about 87 mm, and the distance between the centers of the support means 203a, 203b at the horizontal bars 204a, 204b is only 40 mm. The horizontal bars 204a, 204b extend horizontally and in parallel.

The horizontal bars 204a, 204b are covered with Teflon® and have a circular cross-section with a diameter of 10 mm (including the Teflon). The surface of the horizontal bars is smooth.

The upper fixture 202 includes a holder 206 for attachment to a tensile tester, and a metal wire structure 205. The metal wire structure 205 comprises a horizontal portion for contacting the product 1 when lowered towards the base fixture. The horizontal portion has a length of 140 mm. At its two ends, the horizontal portion is attached to vertically extending wire portions, having a length of 50 mm. Thereafter, the wire portions continue with angled wire portions, also having a length of 50 mm, and leaning towards each other such that the upper ends of the angled wire portions are separated by a distance of 90 mm. The angled wire portions are each followed by a second horizontal wire portion having a length of 50 mm. Finally, the second horizontal wire portions are attached to a fixture member 206. The distance between the second horizontal wire portions at the fixture member 206 is thus 90 mm.

The metal wire has a diameter of 3 mm, and is made of a rigid and inflexible material.

The upper fixture 202 is arranged in relation to the base fixture 201 such that the wire structure 205 is perpendicular to the horizontal supports 204a, 204b.

For testing, the fixtures 201, 202 are mounted to the tensile tester. The upper fixture is adjusted such that the distance between the horizontal metal wire and the uppermost side of the sample when resting on the base 207 of the base fixture is about 2 mm. With this distance, the sample may easily be positioned on the base fixture. The sample shall be positioned such that the upper fixture will impact the middle of the sample.

For testing, the upper fixture is lowered towards the sample with a velocity of 200 mm/min, so as to push the product down between the horizontal supports. The test is finished when the entire product has been pushed down between the supports.

If the article to be tested is provided with an adhesive covered by a release paper, the release paper is removed and the adhesive is powdered with talc so that no stickiness from the adhesive is maintained before testing.

The samples shall be conditioned for at least 4 hours at 23±2° C. and 50±5% relative humidity before testing.

For each test, the maximum force obtained is recorded.

The force obtained when testing is defined as the resistance when the sample resting on the Teflon covered base fixture is folded down into the same by the downwardly moving metal wire of the upper fixture.

Equipment Used:

Tensile tester: e.g. Lloyd LRX

Load cell: 20N

Velocity: 200 mm/min

Thickness Measurement

The thickness of the four products was measured using a conventional method, using a compression pressure of 0.5 kPa.

Results

The flexural rigidity of the side portions and central portions of four products was measured using the method described above.

Before testing, the side portions were cut off from the central portion of each article.

Thereafter, the side portion was placed resting on its longitudinal edge on the horizontal bars of the test equipment, and the wire structure lowered towards the side portion such that the wire structure is perpendicular to the other longitudinal edge of the side portion.

The flexural rigidity of the central portion was measured with the central portion placed flatly on the horizontal bars of the test equipment, with the garment facing side facing downwards. The central portion was placed such that the wire structure extended along the length direction of the central portion, "dividing" the central portion into two longitudinal halves.

The use of the flexural rigidity test as described above in this particular manner is believed to be useful to indicate the requirements of rigidity of the side portions in relation to the rigidity of the central portion in order to achieve folding of the side portions rather than creasing of the side portions and/or the central portion when the product is subject to compression between the thighs of a user. It is understood that the values obtained for the side portions and the central portion are not immediately comparable. In order to have comparable values, it might actually be more suitable to measure also the side portions longitudinally. However, since such a measurement is practically inconvenient, it has been replaced by the above-described measurement where the side portion is placed on its longitudinal edge and transversely compressed. Nevertheless, the selected method is believed to provide values being suitable for evaluating the deformation properties of the product.

The maximum load results appear in Table 1 below.

TABLE 1

| Product no | Central portion—length direction (N) | Side portion—cross direction on edge (N) |
|---|---|---|
| 1 | 7.1 | 0.43 |
| 2 | 8.8 | 0.55 |
| 3 | 7.4 | 0.93 |
| 4 | 9.1 | 0.56 |

The average maximum load for the central portions was found to be 8.1 N which may be compared to the average maximum load in the cross direction for the side portions which was 0.62 N. Hence, in this case the maximum load of the article at the side portions is on average about 7.9% of the maximum load of the article at the central portion as measured herein. On discounting article 3 which shows a slightly different value than the other articles, the values are found to be rather constant about 6.2%. Hence, values between 5.5 and 7% are believed to be particularly useful.

The measurements of maximum load may be sensitive to irregularities in the product and to errors in the test procedure. For example, insufficient provision of talc to an adhesive on the garment facing side of the product might lead to erroneous values, as may creases on the garment facing side of the product.

For testing wider products than the ones described above, longer horizontal bars as well as a longer horizontal wire portion may be used.

Four corresponding products were used for measuring the thickness of the side portions and of the central portion. In this case, the thickness of both of the side portions of each article was measured.

The thickness of the central portion was measured at the centre of the central portion itself, i.e. at the centre of the middle lobe of the entire article. The thickness of the side portions was measured at the centre of each side portion. The thickness measurements shall be performed before cutting the products in pieces for the flexural rigidity test.

The results of the thickness measurements appear in Table 2 below:

TABLE 2

| Product no | Central portion (mm) | $1^{st}$ Side portion (mm) | $2^{nd}$ Side portion (mm) |
|---|---|---|---|
| 1 | 12.0 | 6.6 | 6.7 |
| 2 | 12.1 | 8.1 | 7.1 |
| 3 | 11.3 | 6.7 | 6.1 |
| 4 | 10.4 | 6.4 | 6.3 |

The average thickness for the central portions was found to be 11.45 mm which may be compared to the average thickness for the side portions which was 6.75 mm. Hence, in this case the thickness of the article at the side portions is about 59% of the thickness of the article at the central portion as measured in the cross direction.

Hence, the thickness of the side portions of the measured articles amounts to about 59% of the thickness of the central portions and the flexural rigidity of the side portions is about 7.9% of the flexural rigidity of the central portions (if expressed in maximum load).

It will be understood that several embodiments and variants of the disclosed embodiments are possible. The shape of the absorbent core may be varied, as may the individual shapes of the upper and lower core when two cores are used. The side portions could include material from two cores, and the lengths of the two cores may be varied. The compression lines could be restricted to an upper core and to a surface material, through one core only, or through two cores. Further, additional cores may be used. The materials of different layers of the product may be varied, as may the thickness and layout of different layers.

Further, although the described embodiment is a three-lobe shaped product, it is understood that the idea is applicable to products being differently shaped. References being made in the description to the thickness or flexural rigidity of the central portion at the middle lobe are understood to be equivalent with the thickness or flexural rigidity of the central portion at a location opposite the side portions, in embodiments where there is no "middle" lobe present.

Further, it is understood that the function of several of the features described in relation to the present disclosure, although providing an highly advantageous result when provided in combination, may be used separately in order to achieve the advantages described in relation to each feature.

The invention claimed is:

1. An absorbent article having a length and a width extension, said length being greater than said width, comprising: absorbent core material, the absorbent core material forming a central portion and a pair of longitudinal side portions, wherein a pair of folding lines is provided so as to divide said absorbent core material into said central portion and said pair of longitudinal side portions and a flexural rigidity of the article at the side portions is between 3 and 20% of a flexural rigidity of the article of the central portion at a location opposite the side portions, and wherein each of the pair of longitudinal side portions is located at a respective end of the width extension.

2. The absorbent article according to claim 1, wherein the flexural rigidity of the article at the side portions is between 0.35 and 1.1.

3. The absorbent article according to claim 1, wherein the flexural rigidity of the article at the central portion at a location opposite the side portions is between 6.5 and 10.1.

4. The absorbent article according to claim 1, wherein a thickness of the article at the side portions is less than a thickness of the central portion at a location opposite the side portions.

5. The absorbent article according to claim 4, wherein the thickness of the article at the side portions is between 40 and 80% of the thickness of the article at a location opposite the side portions.

6. The absorbent article according to claim 1, wherein the folding lines are formed by compression of the absorbent material.

7. The absorbent article according to claim 1, wherein the folding lines completely separate the absorbent material in the side portions from the absorbent material in the central portion.

8. The absorbent article according to claim 1, wherein the folding lines only partly separate the absorbent material in the side portions from the absorbent material in the central portion.

9. The absorbent article according to claim 1, wherein the folding lines are positioned and extending along a length such that, when the article is in use, the folding lines are generally positioned so as to extend along the crotch area of a user, starting from the gracilis tendons and ending in the region of the perineum, whereby the side portions may extend from the central portion towards the user so as to form an arc shape as seen in a transversal direction of the article.

10. The absorbent article according to claim 1, wherein the folding lines have a length of about 60 to 170 mm.

11. The absorbent article according to claim 1, wherein the folding lines extend along about ⅓ of the total length of the article.

12. The absorbent article according to claim 1, wherein
outer longitudinal edges of said absorbent material form three convex lobes, said pair of folding lines extend concavely between the longitudinal ends of a middle one of said three lobes, so as to divide the absorbent core material into said central portion and said pair of longitudinal side portions, such that, when the article is in use, the folding lines are generally positioned so as to extend along the crotch area of a user, starting from the gracilis tendons and ending in the region of the perineum, whereby the side portions may extend from the central portion towards the user so as to form an arc shape as seen in a transversal direction of the article.

13. The absorbent article according to claim 12, wherein the length between the longitudinal ends of the middle lobe is about 60 to 270 mm.

14. The absorbent article according to claim 12, wherein the middle lobe extends along about ⅓ of the total length of the article.

15. The absorbent article according to claim 14, wherein each lobe extends along about ⅓ of the total length of the article.

16. The absorbent article according to claim 12, wherein a maximum width of the middle lobe is between 60-150 mm.

17. The absorbent article according to claim 12, wherein a maximum width of the middle lobe divided by a width of one of the ends of said middle lobe is between 110 and 180.

18. The absorbent article according to claim 12, wherein a distance between a maximum width of the middle lobe and an adjacent said folding line is less than 30 mm.

19. The absorbent article according to claim 12, wherein a minimum width of the article is the width as measured at either of the ends of the middle lobe.

20. The absorbent article according to claim 12, wherein the widths at the two ends of the middle lobe are essentially the same.

21. The absorbent article according to claim 12, wherein the widths at the ends of the middle lobe are in the range 30 to 100 mm.

22. The absorbent article according to claim 12, wherein three points positioned on the longitudinal side of the article at the location of a widest portion of each of the three lobes are positioned along a straight line.

23. The absorbent article according to claim 12, wherein maximum widths of the three lobes are substantially the same.

24. The absorbent article according to claim 1, wherein a garment facing side of the article is free from adhesive at the side portions.

25. The absorbent article according to claim 1, wherein the absorbent core material comprises an upper absorbent core and a lower absorbent core.

26. The absorbent article according to claim 25, wherein one of the upper and lower absorbent cores is wider than the other of said upper and lower absorbent cores as measured at the side portions of the article.

27. The absorbent article according to claim 26, wherein the folding lines extend along the longitudinal sides of the least wide of the upper and lower absorbent cores, such that said side portions essentially comprise absorbent material from one of the absorbent cores only.

28. The absorbent article according to claim 27, wherein a thickness of the article at said side portions includes the thickness of only one of the lower absorbent core and the upper absorbent core, and a thickness of the article at the central portion opposite the side portions includes the thickness of the lower absorbent core plus the thickness of the upper absorbent core.

29. The absorbent article according to claim 25, wherein one of the upper and lower absorbent cores is longer than the other one of said upper and lower absorbent cores as measured in the longitudinal direction of the article.

30. The absorbent article according to claim 25, wherein the least wide of the cores as measured at the side portions is generally hour-glass shaped.

31. The absorbent article according to claim 25, wherein the widest one of the cores as measured at the side portions is generally circular or oval.

32. An absorbent article having a length and a width extension, said length being greater than said width, comprising: absorbent core material, the absorbent core material forming a central portion and a pair of longitudinal side portions, wherein a pair of folding lines is provided so as to divide said absorbent core material into said central portion and said pair of longitudinal side portions, and wherein a thickness of the article at the side portions is between 40 and 80% of the thickness of the article at a location opposite the side portions, and wherein each of the pair of longitudinal side portions is located at a respective end of the width extension.

33. An absorbent article having a length and a width extension, said length being greater than said width, comprising:
absorbent core material, the absorbent core material comprising an upper and a lower absorbent core, wherein one of the upper and lower absorbent cores is wider than the other of said upper and lower absorbent cores as measured at side portions of the article,
wherein folding lines extend along the longitudinal sides of the least wide of the upper and lower absorbent cores, such that said side portions comprise absorbent material from one of the absorbent cores only, and
wherein each of the side portions is located at a respective end of the width extension.

* * * * *